(12) United States Patent
Suzuki et al.

(10) Patent No.: US 12,383,443 B2
(45) Date of Patent: Aug. 12, 2025

(54) CONTROL APPARATUS, SYSTEM, VEHICLE, AND MEDICAL EXAMINATION SUPPORT METHOD

(71) Applicant: TOYOTA JIDOSHA KABUSHIKI KAISHA, Toyota (JP)

(72) Inventors: Hiroyuki Suzuki, Miyoshi (JP); Yoshinori Kanemitsu, Tachikawa (JP); Hirohiko Taniguchi, Yokohama (JP); Hirona Ota, Seto (JP); Yuki Tatsumoto, Seto (JP); Keiichi Uno, Aichi-ken (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 299 days.

(21) Appl. No.: 18/152,628

(22) Filed: Jan. 10, 2023

(65) Prior Publication Data
US 2023/0218454 A1 Jul. 13, 2023

(30) Foreign Application Priority Data

Jan. 11, 2022 (JP) ................. 2022-002629

(51) Int. Cl.
| | | |
|---|---|---|
| A61G 3/00 | (2006.01) | |
| G06V 20/58 | (2022.01) | |
| G07C 5/00 | (2006.01) | |
| G16H 40/67 | (2018.01) | |

(52) U.S. Cl.
CPC ........... *A61G 3/001* (2013.01); *G06V 20/584* (2022.01); *G07C 5/008* (2013.01); *G16H 40/67* (2018.01)

(58) Field of Classification Search
CPC ...................................................... A61B 3/001
See application file for complete search history.

(56) References Cited

U.S. PATENT DOCUMENTS

| | | | |
|---|---|---|---|
| 2007/0219468 A1* | 9/2007 | Shah | A61B 5/1112 600/595 |
| 2018/0259959 A1* | 9/2018 | Yamada | G06Q 10/0631 |
| 2018/0348759 A1* | 12/2018 | Freeman | A61N 1/3904 |
| 2020/0353936 A1* | 11/2020 | Salter | B60W 60/00 |
| 2021/0035038 A1 | 2/2021 | Suzuki et al. | |

FOREIGN PATENT DOCUMENTS

| | | |
|---|---|---|
| JP | 63-084518 A | 4/1988 |
| JP | 2010057664 A | 3/2010 |
| JP | 2017064016 A | 4/2017 |
| JP | 2021022332 A | 2/2021 |

\* cited by examiner

*Primary Examiner* — Robert A Sorey
(74) *Attorney, Agent, or Firm* — Dickinson Wright, PLLC

(57) ABSTRACT

A control apparatus includes a controller configured to acquire driving data regarding driving of a vehicle in which a medical examination can be performed, determine a driving condition of the vehicle based on the acquired driving data, and adjust implementation timing of at least one examination item included in the medical examination according to the determined driving condition.

15 Claims, 6 Drawing Sheets

CONTROL APPARATUS, SYSTEM, VEHICLE, AND MEDICAL EXAMINATION SUPPORT METHOD

CROSS-REFERENCE TO RELATED APPLICATION

This application claims priority to Japanese Patent Application No. 2022-002629 filed on Jan. 11, 2022, the entire contents of which are incorporated herein by reference.

TECHNICAL FIELD

The present disclosure relates to a control apparatus, a system, a vehicle, and a medical examination support method.

BACKGROUND

Patent Literature (PTL) 1 discloses a vehicle in which medical examinations can be performed.

CITATION LIST

Patent Literature

PTL 1: JP 2021-022332 A

SUMMARY

When medical examinations are performed in vehicles, some examination items may cause danger due to phenomena such as vibration of the vehicles.

It would be helpful to improve safety when medical examinations are performed in vehicles.

A control apparatus according to the present disclosure includes a controller configured to:
acquire driving data regarding driving of a vehicle in which a medical examination can be performed;
determine a driving condition of the vehicle based on the acquired driving data; and
adjust implementation timing of at least one examination item included in the medical examination according to the determined driving condition.

A medical examination support method according to the present disclosure includes:
acquiring, by a controller, driving data regarding driving of a vehicle in which a medical examination can be performed;
determining, by the controller, a driving condition of the vehicle based on the acquired driving data; and
adjusting, by the controller, implementation timing of at least one examination item included in the medical examination according to the determined driving condition.

According to the present disclosure, safety is improved when medical examinations are performed in vehicles.

BRIEF DESCRIPTION OF THE DRAWINGS

In the accompanying drawings.

DETAILED DESCRIPTION

Figure 1:
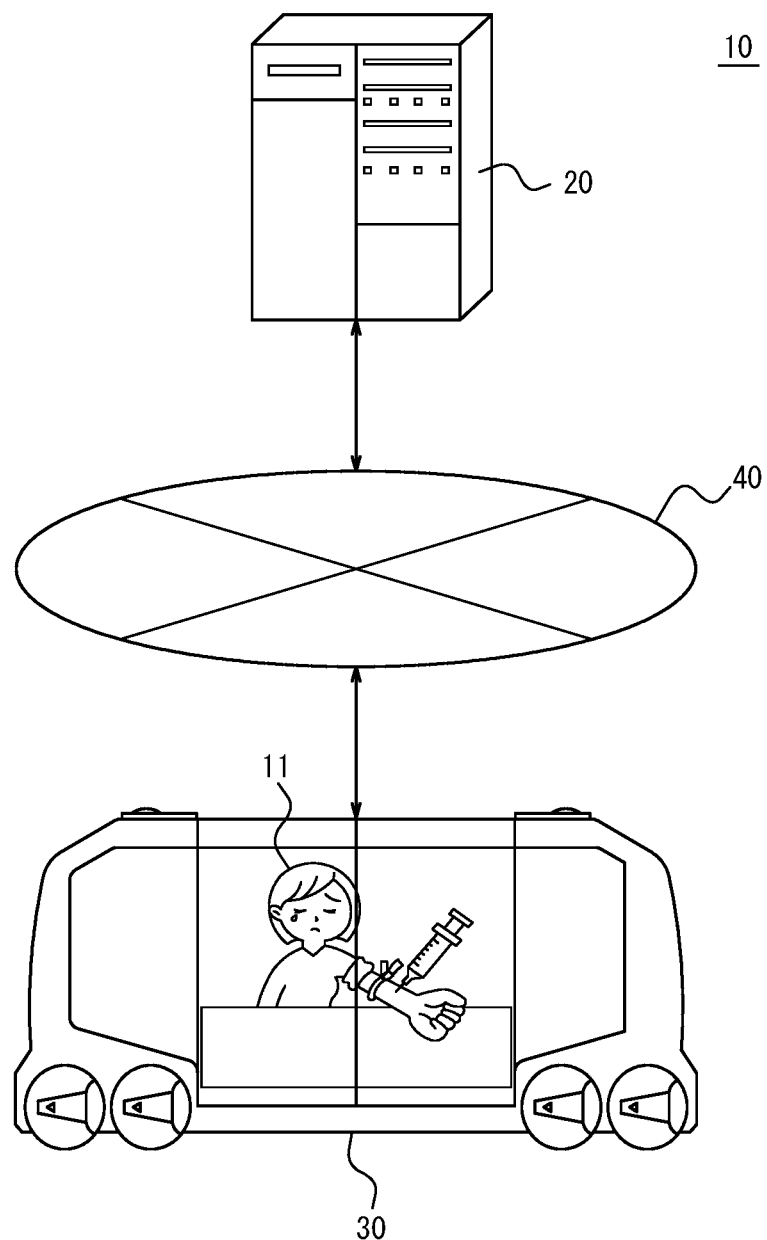
FIG. 1 is a diagram illustrating a configuration of a system according to an embodiment of the present disclosure.

An embodiment of the present disclosure will be described below, with reference to the drawings.

In the drawings, the same or corresponding portions are denoted by the same reference numerals. In the descriptions of the present embodiment, detailed descriptions of the same or corresponding portions are omitted or simplified, as appropriate.

A configuration of a system 10 according to the present embodiment will be described with reference to FIG. 1.

The system 10 according to the present embodiment includes a control apparatus 20 and a vehicle 30 in which medical examinations can be performed. The control apparatus 20 can communicate with the vehicle 30 via a network 40.

The control apparatus 20 is installed in a facility such as a data center. The control apparatus 20 is a computer such as a server that belongs to a cloud computing system or another type of computing system.

The vehicle 30 is equipped with medical examination equipment so that a medical examination can be performed in the vehicle 30. The medical examination includes, as one or more examination items, height measurement, weight measurement, abdominal circumference measurement, vision test, hearing test, blood pressure test, urine collection, blood collection, chest radiography, stomach radiography, ultrasonography, electrocardiography, CT test, MRI test, mammography, osteoporosis test, medical interview, or any combination of the above. The term "CT" is an abbreviation of computed tomography. The term "MRI" is an abbreviation of magnetic resonance imaging. As the medical examination equipment, equipment corresponding to each of the examination items is mounted. In other words, a height meter, a weight meter, vision testing equipment, hearing testing equipment, a blood pressure meter, urinalysis equipment, blood testing equipment, X-ray imaging equipment, ultrasound equipment, an electrocardiograph, CT testing equipment, MRI testing equipment, or any combination of the above may be mounted. As ancillary equipment, a bed on which a user 11 having the medical examination may lie, or a chair on which the user 11 may sit. The vehicle 30 is, for example, any type of automobile such as a gasoline vehicle, a diesel vehicle, a hydrogen vehicle, an HEV, a PHEV, a BEV, or an FCEV. The term "HEV" is an abbreviation of hybrid electric vehicle. The term "PHEV" is an abbreviation of plug-in hybrid electric vehicle. The term "BEV" is an abbreviation of battery electric vehicle. The term "FCEV" is an abbreviation of fuel cell electric vehicle. The vehicle 30, which is an AV in the present embodiment, may be driven by a driver, or the driving may be automated at any level. The term "AV" is an abbreviation of autonomous vehicle. The automation level is, for example, any one of Level 1 to Level 5 according to the level classification defined by SAE. The name "SAE" is an abbreviation of Society of Automotive Engineers. The vehicle 30 may be a MaaS-dedicated vehicle. The term "MaaS" is an abbreviation of Mobility as a Service.

The network 40 includes the Internet, at least one WAN, at least one MAN, or any combination thereof. The term "WAN" is an abbreviation of wide area network. The term "MAN" is an abbreviation of metropolitan area network. The network 40 may include at least one wireless network, at least one optical network, or any combination thereof. The wireless network is, for example, an ad hoc network, a cellular network, a wireless LAN, a satellite communication network, or a terrestrial microwave network. The term "LAN" is an abbreviation of local area network.

An outline of the present embodiment will be described with reference to FIG. 1.

The control apparatus 20 acquires driving data Dd regarding driving of the vehicle 30. The control apparatus 20 determines a driving condition Cd of the vehicle 30 based on the acquired driving data Dd. The control apparatus 20 adjusts, according to the determined driving condition Cd, implementation timing Ti of at least one examination item included in the medical examination to be performed in the vehicle 30.

According to the present embodiment, in the case of performing the medical examination in the vehicle 30, the medical examination can be performed in conjunction with movement of the vehicle 30, such as postponing a blood test using an injection needle when the vehicle 30 is moving at high speed, starting, braking, or traveling on a rough road. A s a result, safety is improved when the medical examination is performed in the vehicle 30.

Figure 2:
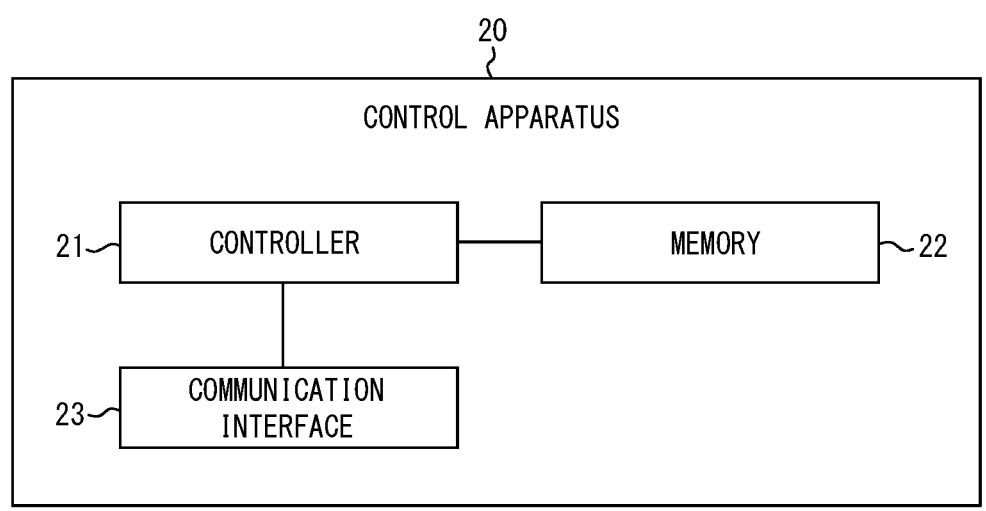
FIG. 2 is a block diagram illustrating a configuration of a control apparatus according to the embodiment of the present disclosure.

A configuration of the control apparatus 20 according to the present embodiment will be described with reference to FIG. 2.

The control apparatus 20 includes a controller 21, a memory 22, and a communication interface 23.

The controller 21 includes at least one processor, at least one programmable circuit, at least one dedicated circuit, or any combination thereof. The processor is a general purpose processor such as a CPU or a GPU, or a dedicated processor that is dedicated to specific processing. The term "CPU" is an abbreviation of central processing unit. The term "GPU" is an abbreviation of graphics processing unit. The programmable circuit is, for example, an FPGA. The term "FPGA" is an abbreviation of field-programmable gate array. The dedicated circuit is, for example, an ASIC. The term "ASIC" is an abbreviation of application specific integrated circuit. The controller 21 executes processes related to operations of the control apparatus 20 while controlling components of the control apparatus 20.

The memory 22 includes at least one semiconductor memory, at least one magnetic memory, at least one optical memory, or any combination thereof. The semiconductor memory is, for example, RAM or ROM. The term "RAM" is an abbreviation of random access memory. The term "ROM" is an abbreviation of read only memory. The RAM is, for example, SRAM or DRAM. The term "SRAM" is an abbreviation of static random access memory. The term "DRAM" is an abbreviation of dynamic random access memory. The ROM is, for example, EEPROM. The term "EEPROM" is an abbreviation of electrically erasable programmable read only memory. The memory 22 functions as, for example, a main memory, an auxiliary memory, or a cache memory. The memory 22 stores data to be used for the operations of the control apparatus 20 and data obtained by the operations of the control apparatus 20.

The communication interface 23 includes at least one interface for communication. The interface for communication is, for example, a LAN interface. The communication interface 23 communicates with the vehicle 30. The communication interface 23 receives data to be used for the operations of the control apparatus 20, and transmits data obtained by the operations of the control apparatus 20.

The functions of the control apparatus 20 are realized by execution of a program according to the present embodiment by a processor serving as the controller 21. That is, the functions of the control apparatus 20 are realized by software. The program causes a computer to execute the operations of the control apparatus 20, thereby causing the computer to function as the control apparatus 20. That is, the computer executes the operations of the control apparatus 20 in accordance with the program to thereby function as the control apparatus 20.

The program can be stored on a non-transitory computer readable medium. The non-transitory computer readable medium is, for example, flash memory, a magnetic recording device, an optical disc, a magneto-optical recording medium, or ROM. The program is distributed, for example, by selling, transferring, or lending a portable medium such as an SD card, a DVD, or a CD-ROM on which the program is stored. The term "SD" is an abbreviation of Secure Digital. The term "DVD" is an abbreviation of digital versatile disc. The term "CD-ROM" is an abbreviation of compact disc read only memory. The program may be distributed by storing the program in a storage of a server and transferring the program from the server to another computer. The program may be provided as a program product.

For example, the computer temporarily stores, in a main memory, a program stored in a portable medium or a program transferred from a server. Then, the computer reads the program stored in the main memory using a processor, and executes processes in accordance with the read program using the processor. The computer may read a program directly from the portable medium, and execute processes in accordance with the program. The computer may, each time a program is transferred from the server to the computer, sequentially execute processes in accordance with the received program. Instead of transferring a program from the server to the computer, processes may be executed by a so-called ASP type service that realizes functions only by execution instructions and result acquisitions. The term "ASP" is an abbreviation of application service provider. Programs encompass information that is to be used for processing by an electronic computer and is thus equivalent to a program. For example, data that is not a direct command to a computer but has a property that regulates processing of the computer is "equivalent to a program" in this context.

Some or all of the functions of the control apparatus 20 may be realized by a programmable circuit or a dedicated circuit serving as the controller 21. That is, some or all of the functions of the control apparatus 20 may be realized by hardware.

Operations of the control apparatus 20 according to the present embodiment will be described with reference to FIG. 3. These operations correspond to a medical examination support method according to the present embodiment.

In step S101, the controller 21 of the control apparatus 20 acquires driving data Dd regarding driving of the vehicle 30. The driving data Dd is specifically acquired in any one of the following two procedures.

In the first procedure, the vehicle 30 transmits positioning results obtained by a GNSS receiver mounted on the vehicle 30 to the control apparatus 20, as position data Dp, two or more times via a communication interface of the vehicle 30, which is compliant with a mobile communication standard such as LTE, the 4G standard, or the 5G standard. The term "LTE" is an abbreviation of Long Term Evolution. The term "4G" is an abbreviation of 4th generation. The term "5G" is an abbreviation of 5th generation. The term "GNSS" is an abbreviation of global navigation satellite system. GNSS is, for example, GPS, QZSS, BDS, GLONASS, or Galileo. The term "GPS" is an abbreviation of Global Positioning System. The term "QZSS" is an abbreviation of Quasi-Zenith Satellite System. QZSS satellites are called quasi-zenith satellites. The term "BDS" is an abbreviation of BeiDou Navigation Satellite System. The term "GLONASS" is an abbreviation of Global Navigation Satellite System. The controller 21 of the control apparatus 20 receives the position data Dp from the vehicle 30 via the communication interface 23. Whenever the controller 21 receives the position data Dp, the controller 21 stores the received position data Dp in the memory 22, thereby accumulating, as the driving data Dd, data Dd1 indicating the position of the vehicle 30 in time series in the memory 22. In other words, the controller 21 acquires the driving data Dd by receiving the data Dd1 indicating the position of the vehicle 30 in time series from the vehicle 30 via the communication interface 23.

In the second procedure, the vehicle 30 transmits a sensing result obtained by a sensor such as a camera, LiDAR, or radar mounted on the vehicle 30, as sensor data Ds, at least once to the control apparatus 20 via the communication interface of the vehicle 30. The term "LiDAR" is an abbreviation of light detection and ranging. The controller 21 of the control apparatus 20 receives the sensor data Ds from the vehicle 30 via the communication interface 23. Upon receiving the sensor data Ds, the controller 21 stores the received sensor data Ds in the memory 22, thereby saving, as the driving data Dd, data Dd2 indicating the sensing result obtained by the sensor mounted on the vehicle 30 in the memory 22. In other words, the controller 21 acquires the driving data Dd by receiving the data Dd2 indicating the sensing result obtained by the sensor mounted on the vehicle 30 from the vehicle 30 via the communication interface 23.

In step S102, the controller 21 of the control apparatus 20 determines a driving condition Cd of the vehicle 30 based on the driving data Dd acquired in step S101. Specifically, the controller 21 determines, as the driving condition Cd, whether the speed of the vehicle 30 exceeds a first threshold value Th1. Whether the speed of the vehicle 30 exceeds the first threshold value Th1 is specifically determined by the following procedure.

When the data Dd1 is acquired as the driving data Dd in step S101, the controller 21 of the control apparatus 20 analyzes a change in position indicated by the acquired data Dd1 to determine whether the speed of the vehicle 30 exceeds the first threshold value Th1. For example, the controller 21 calculates the speed of the vehicle 30 by dividing a distance between the current position of the vehicle 30 and the immediately preceding position thereof, indicated by the acquired data Dd1, by a difference between corresponding two positioning times. The controller 21 then determines whether the calculated speed exceeds the first threshold value Th1.

When the data Dd2 is acquired as the driving data Dd in step S101, the controller 21 of the control apparatus 20 analyzes the sensing result indicated by the acquired data Dd2 to determine whether the speed of the vehicle 30 exceeds the first threshold value Th1. For example, the controller 21 calculates the speed of the vehicle 30 by analyzing video, which corresponds to the acquired data Dd2, captured by the camera mounted on the vehicle 30. The controller 21 then determines whether the calculated speed exceeds the first threshold value Th1. As a video analysis method, a known method can be used. Machine learning, such as deep learning, may be used.

Figure 3:
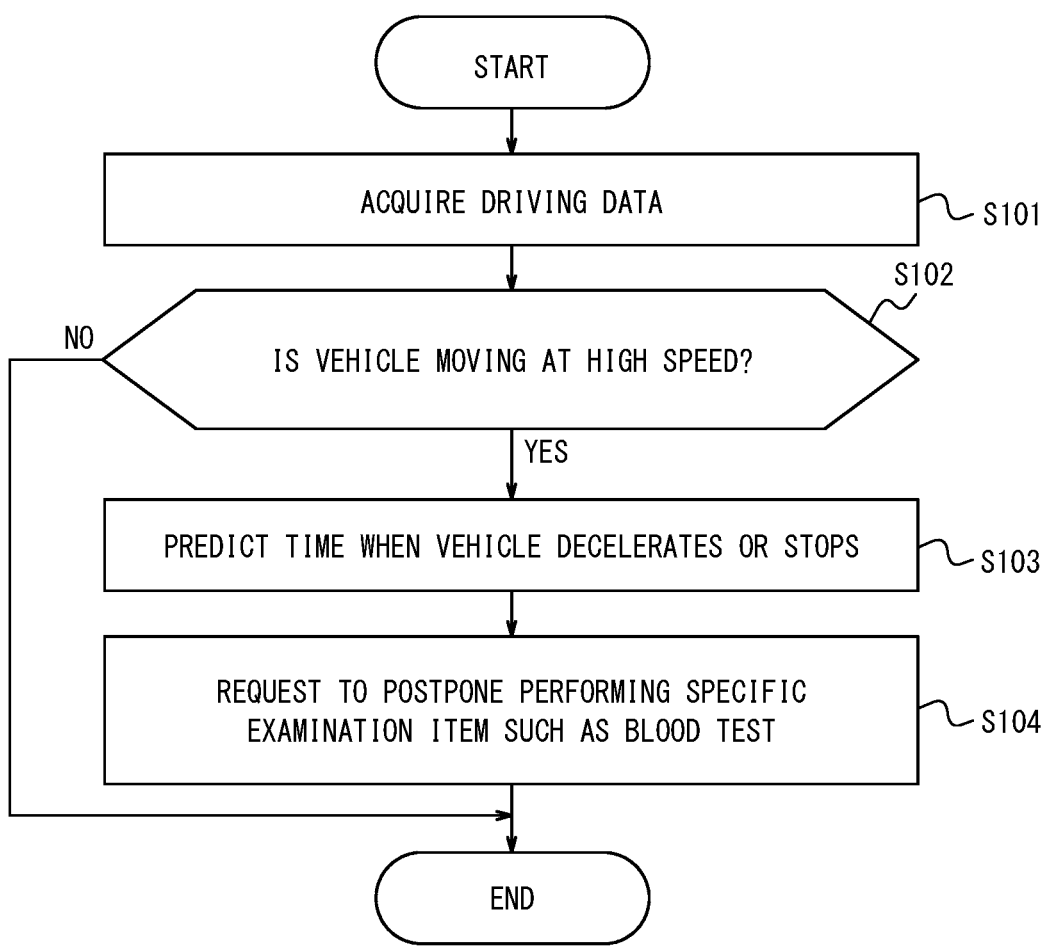
FIG. 3 is a flowchart illustrating operations of the control apparatus according to the embodiment of the present disclosure.

In the operations illustrated in FIG. 3, for example, the first threshold value Th1 is set to a value between 50 km/h and 80 km/h inclusive. Thus, it is possible to determine, as the driving condition Cd, whether the vehicle 30 is moving at high speed. Alternatively, the first threshold value Th1 may be set to 0 km/h. In such an example, it is possible to determine, as the driving condition Cd, whether the vehicle 30 is moving or stopped.

When it is determined in step S102 that the speed of the vehicle 30 exceeds the first threshold value Th1, the process in step S103 is performed. When it is determined in step S102 that the speed of vehicle 30 does not exceed the first threshold value Th1, the operations illustrated in FIG. 3 are ended.

In step S103, the controller 21 of the control apparatus 20 predicts, based on the driving data Dd acquired in step S101, a time Tm1 when the speed of the vehicle 30 comes to be equal to or less than the first threshold value Th1. The time Tm1 is specifically predicted by the following procedure.

When the data Dd1 is acquired as the driving data Dd in step S101, the controller 21 of the control apparatus 20 receives road traffic information such as a speed limit, traffic congestion, or timing of changing a traffic light on a road beyond the current position of the vehicle 30 indicated by the acquired data Dd1 from an external system via the communication interface 23. The controller 21 predicts the time Tm1 when the speed of the vehicle 30 comes to be equal to or less than the first threshold value Th1 with reference to the received road traffic information.

When the data Dd2 is acquired as the driving data Dd in step S101, the controller 21 of the control apparatus 20 generates road traffic information such as a speed limit, traffic congestion, or timing of changing a traffic light on a road beyond the current position of the vehicle 30 by analyzing the video, which corresponds to the acquired data Dd2, captured by the camera mounted on the vehicle 30. As a video analysis method, a known method can be used. Machine learning, such as deep learning, may be used. The controller 21 predicts the time Tm1 when the speed of the vehicle 30 comes to be equal to or less than the first threshold value Th1 with reference to the generated road traffic information.

In step S104, the controller 21 of the control apparatus 20 adjusts, according to the driving condition Cd determined in step S102, implementation timing Ti of at least one examination item included in the medical examination to be performed in the vehicle 30. Specifically, when it is determined in step S102 that the speed of the vehicle 30 exceeds the first threshold value Th1, the controller 21 adjusts the implementation timing Ti by outputting request data Dq requesting to postpone performing the at least one examination item until the speed of the vehicle 30 comes to be equal to or less than the first threshold value Th1. The controller 21 adds data indicating the time Tm1 predicted in step S103 to the request data Dq. The request data Dq is specifically output by the following procedure.

The controller 21 of the control apparatus 20 outputs the request data Dq to the vehicle 30. That is, the controller 21 transmits the request data Dq to the vehicle 30 via the communication interface 23. The vehicle 30 receives the request data Dq from the control apparatus 20 via the communication interface of the vehicle 30. The vehicle 30 displays a text message corresponding to the received request data Dq on a display mounted on the vehicle 30. Alternatively, the vehicle 30 may output an audio message corresponding to the received request data Dq from a speaker mounted on the vehicle 30. The display is, for example, an LCD or an organic EL display. The term "LCD" is an abbreviation of liquid crystal display. The term "EL" is an abbreviation of electro luminescence. The text message to be displayed on the display may include the time Tm1 indicated by the data added to the request data Dq. The message to be output from the speaker may also include the time Tm1.

In one example, the request data Dq includes data requesting to postpone performing a test using an injection needle, such as a blood test, as the at least one examination item. The vehicle 30 displays, according to the request data Dq, a text message such as "Do not perform a blood test because the vehicle is moving at high speed" on the display. Alternatively, the vehicle 30 may output an audio message of similar contents from the speaker. When the time Tm1 is X minutes after the current time, the vehicle 30 may display, on the display, a text message such as "Please perform a blood test in X minutes because the vehicle is moving at high speed". Alternatively, the vehicle 30 may output an audio message of similar contents from the speaker.

According to this example, the examination using the injection needle can be postponed while the vehicle 30 is moving at high speed. As a result, safety is improved when the medical examination is performed in the vehicle 30.

In another example, the request data Dq includes data requesting to postpone performing a test to be performed after the user 11 once stands up, such as a test subsequent to a test performed on the user 11 sitting on a chair, as the at least one examination item. The vehicle 30 displays, according to the request data Dq, a text message such as "Do not let the patient stand up from the chair because the vehicle is moving at high speed" on the display. Alternatively, the vehicle 30 may output an audio message of similar contents from the speaker. When the time Tm1 is X minutes after the current time, the vehicle 30 may display, on the display, a text message such as "Please let the patient stand up from the chair in X minutes because the vehicle is moving at high speed". Alternatively, the vehicle 30 may output an audio message of similar contents from the speaker.

According to this example, it is possible to keep the user 11 from standing up while the vehicle 30 is moving at high speed, especially when the user 11 is an elderly person. As a result, safety is improved when the medical examination is performed in the vehicle 30.

The operations illustrated in FIG. 3 are repeated periodically or whenever a specific event occurs, such as a change in the driving condition of the vehicle 30.

In step S101, the controller 21 of the control apparatus 20 may acquire, as the driving data Dd, data Dd3 indicating the speed of the vehicle 30. Specifically, the controller 21 may receive the data Dd3 indicating the speed of the vehicle 30 from the vehicle 30 via the communication interface 23. In this case, in step S102, the controller 21 simply determines whether the speed indicated by the acquired data Dd3 exceeds the first threshold value Th1.

The process in step S103 may be omitted. In other words, the request data Dq output in step S104 need not be added with data indicating the time Tm1 when the speed of the vehicle 30 comes to be equal to or less than the first threshold value Th1.

In step S104, the controller 21 of the control apparatus 20 may output the request data Dq to a terminal apparatus of a medical staff, such as a nurse, performing the medical examination. In other words, the controller 21 may transmit the request data Dq to the terminal apparatus of the medical staff via the communication interface 23. The terminal apparatus is, for example, a mobile device such as a mobile phone, a smartphone, or a tablet, or a PC. The term "PC" is an abbreviation of personal computer. The terminal apparatus receives the request data Dq from the control apparatus 20 via a communication interface of the terminal apparatus compliant with a mobile communication standard such as LTE, the 4G standard, or the 5G standard. The terminal apparatus displays, on a display of the terminal apparatus, a text message according to the received request data Dq. Alternatively, the terminal apparatus may output an audio message corresponding to the received request data Dq from a speaker of the terminal apparatus.

A variation of the operations illustrated in FIG. 3 will be described with reference to FIG. 4. The process in step S201 is the same as the process in step S101 of FIG. 3, and thus a description thereof is omitted.

In step S202, the controller 21 of the control apparatus 20 determines a driving condition Cd of the vehicle 30 based on the driving data Dd acquired in step S201. Specifically, the controller 21 determines, as the driving condition Cd, whether the acceleration of the vehicle 30 transitorily exceeds a second threshold value Th2. Whether the acceleration of the vehicle 30 transitorily exceeds the second threshold value Th2 is specifically determined by the following procedure.

When the data Dd1 is acquired as the driving data Dd in step S201, the controller 21 of the control apparatus 20 analyzes a change in position indicated by the acquired data Dd1 to determine whether the acceleration of the vehicle 30 transitorily exceeds the second threshold value Th2. For example, the controller 21 determines whether the current position of the vehicle 30 and the immediately preceding position thereof, indicated by the acquired data Dd1, are the same, that is, whether the vehicle 30 is stopped. When it is determined that the vehicle 30 is stopped, the controller 21 refers to map data Dm and determines whether there is a traffic light at the current position of the vehicle 30, in other words, whether the vehicle 30 is waiting for the traffic light to change. When it is determined that the vehicle 30 is waiting for the traffic light to change, the controller 21 determines that the acceleration of the vehicle 30 transitorily exceeds the second threshold value Th2, in other words, the vehicle 30 starts or in some cases accelerates rapidly when the traffic light changes. The map data Dm may be stored in advance in the memory 22 of the control apparatus 20, or may be accumulated in an external system such as an Internet-based GIS. The term "GIS" is an abbreviation of geographic information system.

When the data Dd2 is acquired as the driving data Dd in step S201, the controller 21 of the control apparatus 20 analyzes the sensing result indicated by the acquired data Dd2 to determine whether the acceleration of the vehicle 30 transitorily exceeds the second threshold value Th2. For example, the controller 21 analyzes the video captured by the camera mounted on the vehicle 30, which corresponds to the acquired data Dd2, to determine whether the vehicle 30 is waiting at a traffic light to change. When it is determined that the vehicle 30 is waiting for the traffic light to change, the controller 21 determines that the acceleration of the vehicle 30 transitorily exceeds the second threshold value Th2, in other words, the vehicle 30 starts or in some cases accelerates rapidly when the traffic light changes. As a video analysis method, a known method can be used. Machine learning, such as deep learning, may be used.

Figure 4:
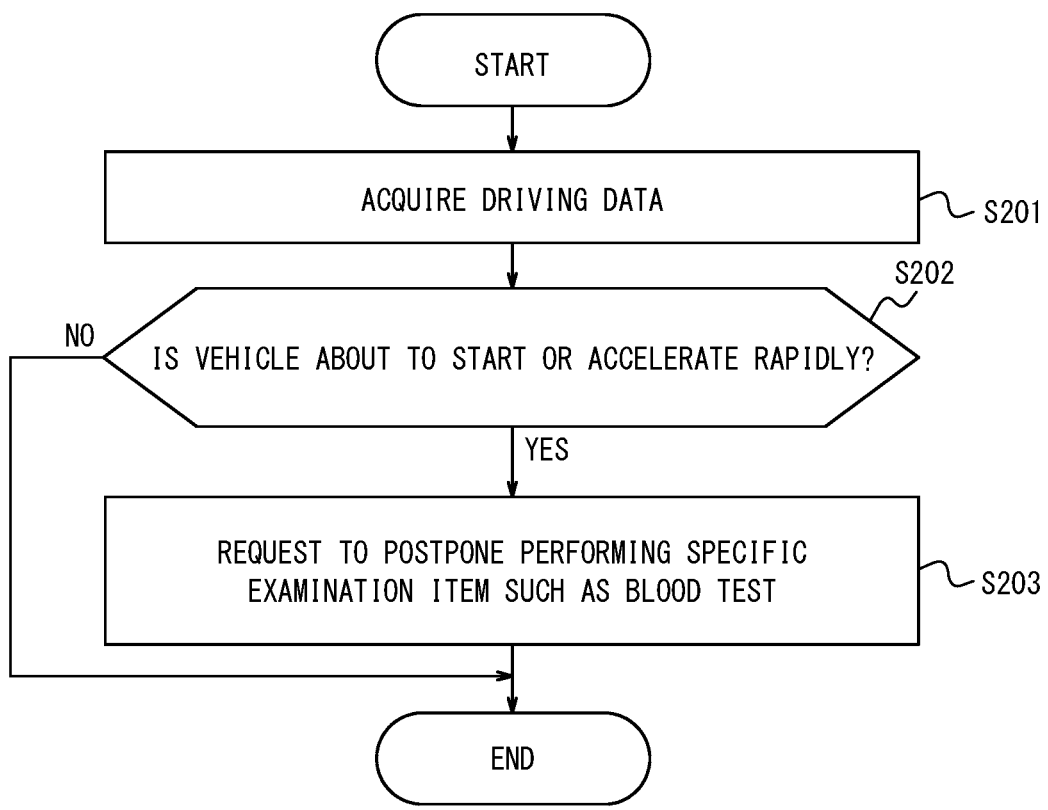
FIG. 4 is a flowchart illustrating a variation of the operations of the control apparatus according to the embodiment of the present disclosure.

In the operations illustrated in FIG. 4, for example, the second threshold value Th2 is set to a value equal to or more than 8 km/h/s and less than 10 km/h/s. Therefore, whether the vehicle 30 is about to start can be determined as the driving condition Cd. Alternatively, the second threshold value Th2 may be set to a value equal to or more than 10 km/h/s. In such an example, whether the vehicle 30 is about to accelerate rapidly can be determined as the driving condition Cd.

When it is determined in step S202 that the acceleration of the vehicle 30 transitorily exceeds the second threshold value Th2, the process in step S203 is performed. When it is determined in step S202 that the acceleration of the vehicle 30 does not exceed the second threshold value Th2, the operations illustrated in FIG. 4 are ended.

In step S203, the controller 21 of the control apparatus 20 adjusts, according to the driving condition Cd determined in step S202, implementation timing Ti of at least one examination item included in the medical examination to be performed in the vehicle 30. Specifically, when it is determined in step S202 that the acceleration of the vehicle 30 transitorily exceeds the second threshold value Th2, the controller 21 adjusts the implementation timing Ti by outputting request data Dq requesting to postpone performing the at least one examination item until the acceleration of the vehicle 30 comes to be equal to or less than the second threshold value Th2 again. A specific procedure for outputting the request data Dq is the same as the procedure in step S104 of FIG. 3, so a description thereof is omitted.

In one example, the request data Dq includes data requesting to postpone performing a test using an injection needle, such as a blood test, as the at least one examination item. The vehicle 30 displays, according to the request data Dq, a text message such as "Do not perform a blood test because the vehicle is about to start" on the display. Alternatively, the vehicle 30 may output an audio message of similar contents from the speaker.

According to this example, the examination using the injection needle can be postponed while the vehicle 30 is starting. As a result, safety is improved when the medical examination is performed in the vehicle 30.

In another example, the request data Dq includes data requesting to postpone performing a test to be performed after the user 11 once stands up, such as a test subsequent to a test performed on the user 11 sitting on a chair, as the at least one examination item. The vehicle 30 displays, according to the request data Dq, a text message such as "Do not let the patient stand up from the chair because the vehicle is about to start" on the display. Alternatively, the vehicle 30 may output an audio message of similar contents from the speaker.

According to this example, it is possible to keep the user 11 from standing up while the vehicle 30 is starting, especially when the user 11 is an elderly person. As a result, safety is improved when the medical examination is performed in the vehicle 30.

The operations illustrated in FIG. 4 are repeated periodically or whenever a specific event occurs, such as a change in the driving condition of the vehicle 30.

In step S203, as in step S104 of FIG. 3, the controller 21 of the control apparatus 20 may output the request data Dq to the terminal apparatus of the medical staff.

Another variation of the operations illustrated in FIG. 3 will be described with reference to FIG. 5. The process in step S301 is the same as the process in step S101 of FIG. 3, and thus a description thereof is omitted.

In step S302, the controller 21 of the control apparatus 20 determines a driving condition Cd of the vehicle 30 based on the driving data Dd acquired in step S301. Specifically, the controller 21 determines, as the driving condition Cd, whether the deceleration of the vehicle 30 transitorily exceeds a third threshold value Th3. Whether the deceleration of the vehicle 30 transitorily exceeds the third threshold value Th3 is specifically determined by the following procedure.

When the data Dd1 is acquired as the driving data Dd in step S301, the controller 21 of the control apparatus 20 analyzes a change in position indicated by the acquired data Dd1 to determine whether the deceleration of the vehicle 30 transitorily exceeds the third threshold value Th3. For example, the controller 21 determines whether the current position of the vehicle 30 and the immediately preceding position thereof, indicated by the acquired data Dd1, are different, that is, whether the vehicle 30 is moving. When it is determined that the vehicle 30 is moving, the controller 21 refers to map data Dm and determines whether there is a traffic light beyond the current position of the vehicle 30. When it is determined that there is a traffic light beyond the current position of the vehicle 30, the controller 21 receives road traffic information, such as timing of changing the traffic light, from an external system via the communication interface 23. The controller 21 refers to the received road traffic information and determines whether the vehicle 30 stops or in some cases decelerates rapidly at the traffic light, in other words, whether the deceleration of the vehicle 30 transitorily exceeds the third threshold value Th3.

When the data Dd2 is acquired as the driving data Dd in step S301, the controller 21 of the control apparatus 20 analyzes the sensing result indicated by the acquired data Dd2 to determine whether the deceleration of the vehicle 30 transitorily exceeds the third threshold value Th3. For example, the controller 21 analyzes the video captured by the camera mounted on the vehicle 30, which corresponds to the acquired data Dd2, to determine whether the vehicle 30 is moving, there is a traffic light beyond the current position of the vehicle 30, and the vehicle 30 stops or in some cases decelerates rapidly at the traffic light, in other words, whether the deceleration of the vehicle 30 transitorily exceeds the third threshold value Th3. As a video analysis method, a known method can be used. Machine learning, such as deep learning, may be used.

Figure 5:
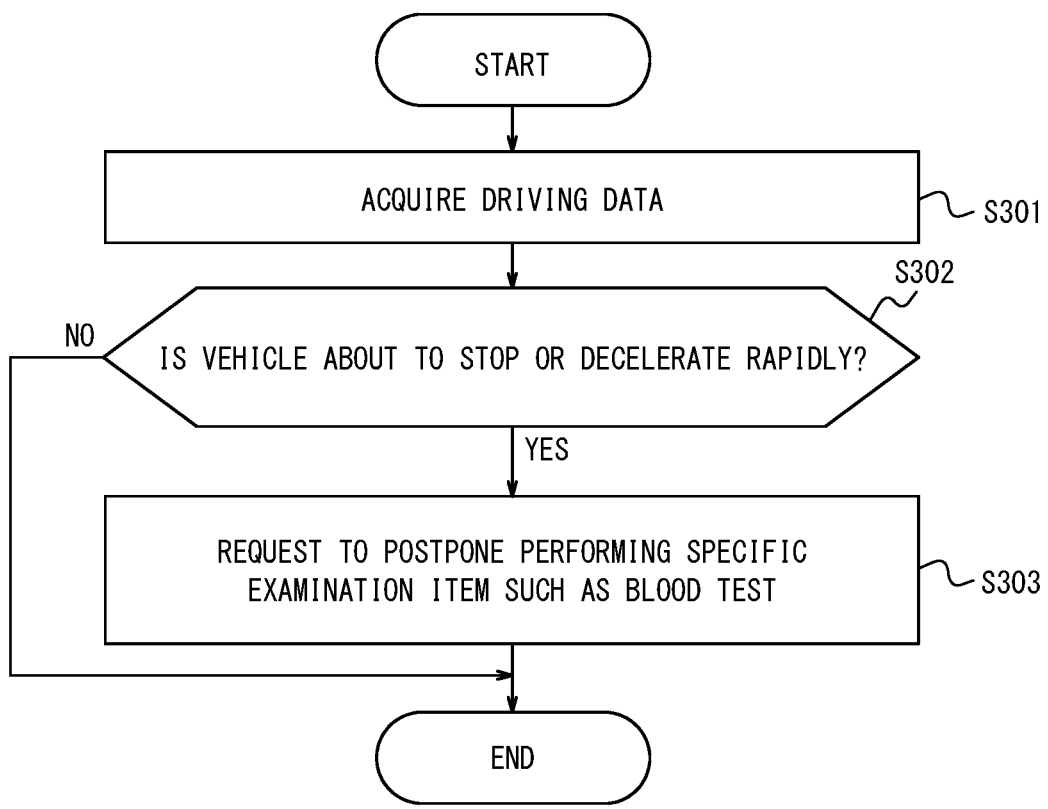
FIG. 5 is a flowchart illustrating another variation of the operations of the control apparatus according to the embodiment of the present disclosure.

In the operations illustrated in FIG. 5, for example, the third threshold value Th3 is set to a value equal to or more than 8 km/h/s and less than 10 km/h/s. Therefore, whether the vehicle 30 is about to stop can be determined as the driving condition Cd. Alternatively, the third threshold value Th3 may be set to a value equal to or more than 10 km/h/s. In such an example, whether the vehicle 30 is about to decelerate rapidly can be determined as the driving condition Cd.

When it is determined in step S302 that the deceleration of the vehicle 30 transitorily exceeds the third threshold value Th3, the process in step S303 is performed. When it is determined in step S302 that the deceleration of the vehicle 30 does not exceed the third threshold value Th3, the operations illustrated in FIG. 5 are ended.

In step S303, the controller 21 of the control apparatus 20 adjusts, according to the driving condition Cd determined in step S302, implementation timing Ti of at least one examination item included in the medical examination to be performed in the vehicle 30. Specifically, when it is determined in step S302 that the deceleration of the vehicle 30 transitorily exceeds the third threshold value Th3, the controller 21 adjusts the implementation timing Ti by outputting request data Dq requesting to postpone performing the at least one examination item until the deceleration of the vehicle 30 comes to be equal to or less than the third threshold value Th3 again. A specific procedure for outputting the request data Dq is the same as the procedure in step S104 of FIG. 3, so a description thereof is omitted.

In one example, the request data Dq includes data requesting to postpone performing a test using an injection needle, such as a blood test, as the at least one examination item. The vehicle 30 displays, according to the request data Dq, a text message such as "Do not perform a blood test because the vehicle is about to stop" on the display. Alternatively, the vehicle 30 may output an audio message of similar contents from the speaker.

According to this example, the examination using the injection needle can be postponed while the vehicle 30 is braking. As a result, safety is improved when the medical examination is performed in the vehicle 30.

In another example, the request data Dq includes data requesting to postpone performing a test to be performed after the user 11 once stands up, such as a test subsequent to a test performed on the user 11 sitting on a chair, as the at least one examination item. The vehicle 30 displays, according to the request data Dq, a text message such as "Do not let the patient stand up from the chair because the vehicle is about to stop" on the display. Alternatively, the vehicle 30 may output an audio message of similar contents from the speaker.

According to this example, it is possible to keep the user 11 from standing up while the vehicle 30 is braking, especially when the user 11 is an elderly person. As a result, safety is improved when the medical examination is performed in the vehicle 30.

The operations illustrated in FIG. 5 are repeated periodically or whenever a specific event occurs, such as a change in the driving condition of the vehicle 30.

In step S303, as in step S104 of FIG. 3, the controller 21 of the control apparatus 20 may output the request data Dq to the terminal apparatus of the medical staff.

Further another variation of the operations illustrated in FIG. 3 will be described with reference to FIG. 6. The process in step S401 is the same as the process in step S101 of FIG. 3, and thus a description thereof is omitted.

In step S402, the controller 21 of the control apparatus 20 determines a driving condition Cd of the vehicle 30 based on driving data Dd acquired in step S401. Specifically, the controller 21 determines, as the driving condition Cd, a road surface condition Rc of a road on which the vehicle 30 travels. The road surface condition Rc is specifically determined by the following procedure.

When the data Dd1 is acquired as the driving data Dd in step S401, the controller 21 of the control apparatus 20 analyzes a change in position indicated by the acquired data Dd1 and identifies a road on which the vehicle 30 travels, to determine the road surface condition Rc of the identified road. For example, the controller 21 determines whether the current position of the vehicle 30 and the immediately preceding position thereof, indicated by the acquired data Dd1, are different, that is, whether the vehicle 30 is moving.

When it is determined that the vehicle 30 is moving, the controller 21 identifies a road beyond the current position of the vehicle 30 with reference to map data Dm. The controller 21 then determines the road surface condition Rc of the identified road with reference to information included in the map data Dm and information obtained from an external system.

When the data Dd2 is acquired as the driving data Dd in step S401, the controller 21 of the control apparatus 20 analyzes the sensing result indicated by the acquired data Dd2 to determine the road surface condition Rc of the road on which the vehicle 30 travels. For example, the controller 21 analyzes point group data, which corresponds to the acquired data Dd2, obtained by LiDAR mounted on the vehicle 30, to determine the road surface condition Rc of the road beyond the current position of the vehicle 30. As a point group data analysis method, a known method can be used. Machine learning, such as deep learning, may be used.

Figure 6:
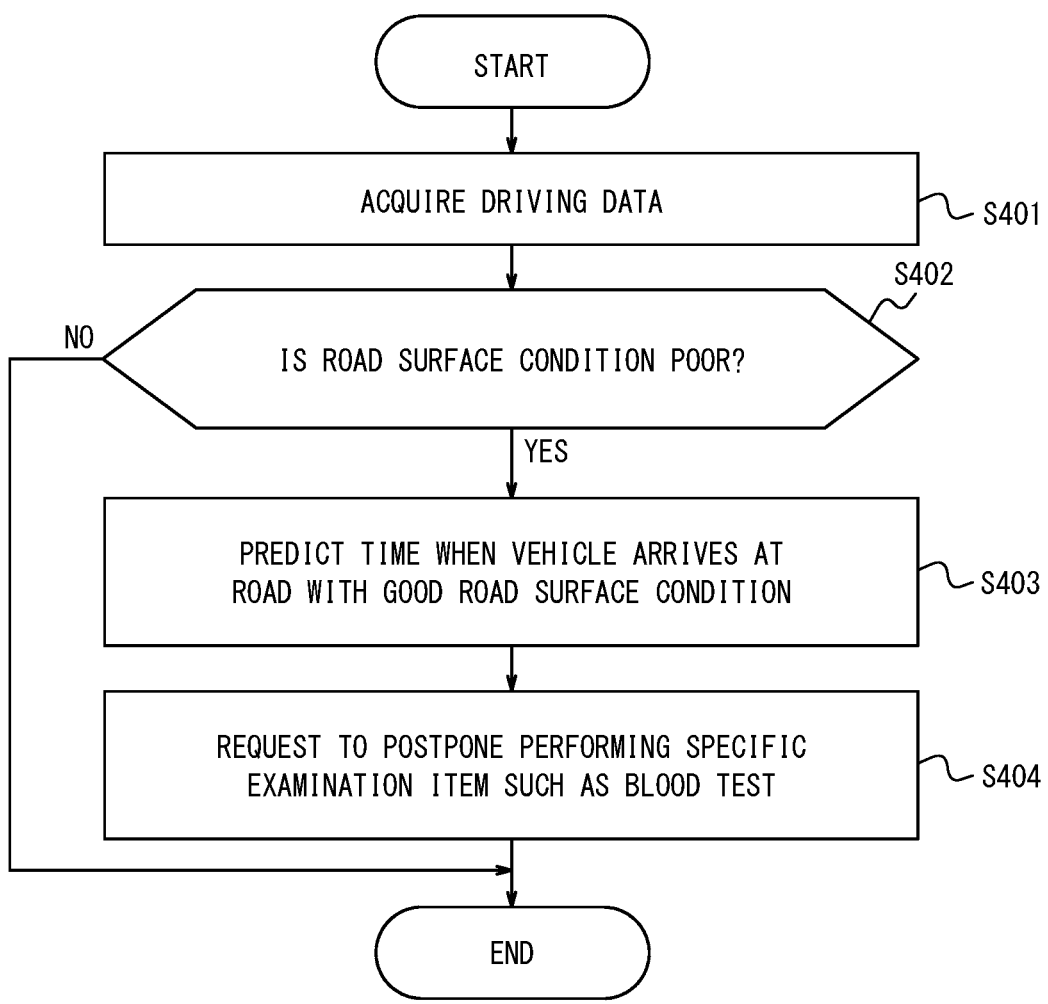
FIG. 6 is a flowchart illustrating yet another variation of the operations of the control apparatus according to the embodiment of the present disclosure.

In the operations illustrated in FIG. 6, the road surface condition Rc is determined depending on whether the road meets a certain criterion, such as being paved.

When the road surface condition Rc determined in step S402 does not meet the criterion, the process in step S403 is performed. When the road surface condition Rc determined in step S402 meets the criterion, the operations illustrated in FIG. 6 are ended.

In step S403, the controller 21 of the control apparatus 20 predicts, based on the driving data Dd acquired in step S401, a time Tm4 when the vehicle 30 arrives at a road meeting the criterion. The time Tm4 is specifically predicted by the following procedure.

When the data Dd1 is acquired as the driving data Dd in step S401, the controller 21 of the control apparatus 20 identifies a group of roads further ahead of the road beyond the current position of the vehicle 30 with reference to the map data Dm. The controller 21 identifies a road that meets the criterion from among the identified group of roads with reference to information included in the map data Dm or information obtained from an external system. The controller 21 receives, from an external system via the communication interface 23, road traffic information such as a speed limit, traffic congestion, or timing of changing a traffic light on each road between the current position of the vehicle 30 indicated by the acquired data Dd1 and the road meeting the criterion. The controller 21 predicts the time Tm4 when the vehicle 30 arrives at the road meeting the criterion, with reference to the received road traffic information.

When the data Dd2 is acquired as the driving data Dd in step S401, the controller 21 of the control apparatus 20 identifies a road that is further ahead of the road beyond the current position of the vehicle 30 and that meets the criterion by analyzing the point group data, which corresponds to the acquired data Dd2, obtained by the LiDAR mounted on the vehicle 30, and generates road traffic information such as a speed limit, traffic congestion, or timing of changing a traffic light on each road between the current position of the vehicle 30 and the road meeting the criterion. As a point group data analysis method, a known method can be used. Machine learning, such as deep learning, may be used. The controller 21 predicts the time Tm4 when the vehicle 30 arrives at the road meeting the criterion, with reference to the generated road traffic information.

In step S404, the controller 21 of the control apparatus 20 adjusts, according to the driving condition Cd determined in step S402, implementation timing Ti of at least one examination item included in the medical examination to be performed in the vehicle 30. Specifically, when the road surface condition Rc determined in step S402 does not meet the criterion, the controller 21 adjusts the implementation timing Ti by outputting request data Dq requesting to postpone performing the at least one examination item until the vehicle 30 arrives at the road meeting the criterion. The controller 21 adds data indicating the time Tm4 predicted in step S403 to the request data Dq. The request data Dq is specifically output by the following procedure.

The controller 21 of the control apparatus 20 outputs the request data Dq to the vehicle 30. That is, the controller 21 transmits the request data Dq to the vehicle 30 via the communication interface 23. The vehicle 30 receives the request data Dq from the control apparatus 20 via the communication interface of the vehicle 30. The vehicle 30 displays a text message corresponding to the received request data Dq on the display mounted on the vehicle 30. Alternatively, the vehicle 30 may output an audio message corresponding to the received request data Dq from the speaker mounted on the vehicle 30. The text message displayed on the display may include the time Tm4 indicated by the data added to the request data Dq. The message to be output from the speaker may also include the time Tm4.

In one example, the request data Dq includes data requesting to postpone performing a test using an injection needle, such as a blood test, as the at least one examination item. The vehicle 30 displays, according to the request data Dq, a text message such as "Do not perform a blood test because the vehicle is about to travel on a rough road" on the display. Alternatively, the vehicle 30 may output an audio message of similar contents from the speaker. When the time Tm4 is X minutes after the current time, the vehicle 30 may display, on the display, a text message such as "Please perform a blood test in X minutes because the vehicle is about to travel on a rough road". Alternatively, the vehicle 30 may output an audio message of similar contents from the speaker.

According to this example, the examination using the injection needle can be postponed while the vehicle 30 is traveling on a rough road. As a result, safety is improved when the medical examination is performed in the vehicle 30.

In another example, the request data Dq includes data requesting to postpone performing a test to be performed after the user 11 once stands up, such as a test subsequent to a test performed on the user 11 sitting on a chair, as the at least one examination item. The vehicle 30 displays, according to the request data Dq, a text message such as "Do not let the patient stand up from the chair because the vehicle is about to travel on a rough road" on the display. Alternatively, the vehicle 30 may output an audio message of similar contents from the speaker. When the time Tm4 is X minutes after the current time, the vehicle 30 may display, on the display, a text message such as "Please let the patient stand up from the chair in X minutes because the vehicle is about to travel on a rough road". Alternatively, the vehicle 30 may output an audio message of similar contents from the speaker.

According to this example, it is possible to keep the user 11 from standing up while the vehicle 30 is traveling on a rough road, especially when the user 11 is an elderly person. As a result, safety is improved when the medical examination is performed in the vehicle 30.

The operations illustrated in FIG. 6 are repeated periodically or whenever a specific event occurs, such as a change in the driving condition of the vehicle 30.

The process in step S403 may be omitted. In other words, the request data Dq output in step S404 need not be added with data indicating the time Tm4 when the vehicle 30 arrives at the road meeting the criterion.

In step S404, as in step S104 of FIG. 3, the controller 21 of the control apparatus 20 may output the request data Dq to the terminal apparatus of the medical staff.

As a variation of the present embodiment, the controller 21 of the control apparatus 20 may further acquire route data Dr indicating a route along which the vehicle 30 is to move. The controller 21 may set, based on the acquired route data Dr, implementation order of two or more examination items included in the medical examination to be performed in the vehicle 30.

For example, the vehicle 30 transmits, as the route data Dr, data indicating a route to a destination, such as a hospital, set in navigation equipment installed in the vehicle 30 to the control apparatus 20 via the communication interface of the vehicle 30. The controller 21 of the control apparatus 20 acquires the route data Dr by receiving the route data Dr from the vehicle 30 via the communication interface 23. The controller 21 determines, as with the procedure in step S402 of FIG. 6, a road surface condition of each road included in the route indicated by the acquired route data Dr. The controller 21 optimizes the implementation order of the two or more examination items included in the medical examination, so that some examination items that may cause danger, such as a test using an injection needle or a test to be performed after the user 11 once stands up, are not performed while the vehicle 30 is traveling on a rough road.

As a further variation, the controller 21 of the control apparatus 20 may acquire evaluation data De indicating an evaluation by the user 11 when the vehicle 30 travels on each road included in the route indicated by the route data Dr. The controller 21 may refer to the acquired evaluation data De to set implementation order of examination items in the next medical examination. For example, suppose that the evaluation by the user 11, while the vehicle 30 travels on a certain road, is poor such as dissatisfaction because vibration of the vehicle 30 causes more pain by an injection needle. In this case, even if a road surface condition of the road is determined to be good, the controller 21 may optimize the implementation order of the examination items in the next medical examination so that a test using an injection needle is not performed while the vehicle 30 travels on the road.

The present disclosure is not limited to the embodiment described above. For example, two or more blocks described in the block diagrams may be integrated, or a block may be divided. Instead of executing two or more steps described in the flowcharts in chronological order in accordance with the description, the steps may be executed in parallel or in a different order according to the processing capability of the apparatus that executes each step, or as required. Other modifications can be made without departing from the spirit of the present disclosure.

For example, the control apparatus 20 may be included in the vehicle 30.

The invention claimed is:

1. A control apparatus comprising a controller configured to:

acquire positioning results obtained by a global navigation satellite system receiver mounted on a vehicle in which a medical examination can be performed or sensing results obtained by at least one sensor mounted on the vehicle selected from the group consisting of a camera, LiDAR and radar;

analyze the acquired positioning or sensing results to determine whether a speed of the vehicle exceeds a threshold value; and upon determining that the speed of the vehicle exceeds the threshold value:
- automatically receive, from an external system, or generate, by analyzing the sensing results, road traffic information including a speed limit, a traffic congestion, or a traffic light timing on a road beyond a current position of the vehicle;
- predict, based on the automatically received or generated road traffic information, a time when the speed of the vehicle becomes equal to or less than the threshold value; and
- output, through a display or a speaker in the vehicle, a message requesting a postponement of at least one examination item included in the medical examination.

2. The control apparatus according to claim 1, wherein the at least one examination item includes a test using an injection needle.

3. The control apparatus according to claim 1, wherein the at least one examination item includes a test to be performed after a user who is having the medical examination once stands up.

4. A system comprising:
the control apparatus according to claim 1; and
the vehicle.

5. A vehicle comprising the control apparatus according to claim 1.

6. A control apparatus comprising a controller configured to:
acquire positioning results obtained by a global navigation satellite system receiver mounted on a vehicle in which a medical examination can be performed or sensing results obtained by at least one sensor mounted on the vehicle selected from the group consisting of a camera, LiDAR and radar;

analyze the acquired positioning or sensing results to determine whether the vehicle is waiting for a traffic light to change or whether the vehicle is moving, there is a traffic light beyond a current position of the vehicle, and the vehicle is to stop at the traffic light;

upon determining that the vehicle is waiting for a traffic light to change, output, through a display or a speaker in the vehicle, a message requesting postponement of at least one examination item included in the medical examination until the vehicle starts; and upon determining that the vehicle is moving, there is a traffic light beyond the current position of the vehicle, and the vehicle is to stop at the traffic light, output, through the display or the speaker in the vehicle, a message requesting a postponement of the at least one examination item until the vehicle stops.

7. The control apparatus according to claim 6, wherein the at least one examination item includes a test using an injection needle.

8. The control apparatus according to claim 6, wherein the at least one examination item includes a test to be performed after a user who is having the medical examination once stands up.

9. A system comprising:
the control apparatus according to claim 6; and
the vehicle.

10. A vehicle comprising the control apparatus according to claim 6.

11. A control apparatus comprising a controller is configured to:
acquire positioning results obtained by a global navigation satellite system receiver mounted on a vehicle in which a medical examination can be performed or sensing results obtained by a sensor mounted on the vehicle selected from the group consisting of a camera, LiDAR and radar;

analyze the acquired positioning or sensing results to determine a road surface condition of a road beyond a current position of the vehicle; and upon determining that the determined road surface condition does not meet a criterion:
- identify, based on map data or the sensing results, a road that is further ahead of the road beyond the current position of the vehicle and that meets the criterion;
- automatically receive, from an external system, or generate, by analyzing the sensing results, road traffic information including a speed limit, a traffic congestion, or a traffic light timing on each road between the current position of the vehicle and the identified road that meets the criterion;

predict, based on the automatically received or generated road traffic information, a time when the vehicle arrives at the identified road that meets the criterion; and output, through a display or a speaker in the vehicle, a message requesting a postponement of at least one examination item included in the medical examination until the predicted time.

12. The control apparatus according to claim 11, wherein the at least one examination item includes a test using an injection needle.

13. The control apparatus according to claim 11, wherein the at least one examination item includes a test to be performed after a user who is having the medical examination once stands up.

14. A system comprising:
the control apparatus according to claim 11; and
the vehicle.

15. A vehicle comprising the control apparatus according to claim 11.

* * * * *